(12) United States Patent
Hosomi et al.

(10) Patent No.: US 8,889,359 B2
(45) Date of Patent: Nov. 18, 2014

(54) METHOD AND KIT FOR AMPLIFYING AND DETECTING POLYNUCLEOTIDE USING A MODIFIED TTH POLYMERASE

(75) Inventors: Toshiya Hosomi, Kyoto (JP); Mitsuharu Hirai, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 41 days.

(21) Appl. No.: 13/545,756

(22) Filed: Jul. 10, 2012

(65) Prior Publication Data

US 2013/0017542 A1    Jan. 17, 2013

(30) Foreign Application Priority Data

Jul. 12, 2011    (JP) ................. 2011-153455

(51) Int. Cl.
*C12Q 1/68* (2006.01)
*C12N 9/02* (2006.01)

(52) U.S. Cl.
CPC .............. *C12Q 1/6844* (2013.01); *C12Q 1/686* (2013.01)
USPC .......................................... 435/6.12; 435/194

(58) Field of Classification Search
None
See application file for complete search history.

(56) References Cited

U.S. PATENT DOCUMENTS

| 5,418,149 | A | 5/1995 | Gelfand et al. |
| 5,466,591 | A | 11/1995 | Abramson et al. |
| 5,616,494 | A | 4/1997 | Barnes |
| 2007/0121704 | A1* | 5/2007 | Begero et al. ................. 374/208 |
| 2007/0212704 | A1* | 9/2007 | Dong et al. ........................ 435/6 |

FOREIGN PATENT DOCUMENTS

| EP | 1152062 A2 | 11/2001 |
| EP | 1152062 A2 | 12/2001 |
| JP | 06-502303 A | 3/1994 |
| JP | 2886842 B2 | 4/1999 |
| JP | 3392863 B2 | 3/2003 |
| WO | 03/048309 A2 | 6/2003 |
| WO | 2005/083068 A2 | 9/2005 |

OTHER PUBLICATIONS

Extended European Search Report issued in corresponding European Patent Application No. 12176175.3 dated Oct. 2, 2012.
Baar et al., "Molecular breeding of polymerases for resistance to environmental inhibitors," Nucleic Acids Research, 39: e51 (2011).
Sauter et al., "Evolving Thermostable Reverse Transcriptase Activity in a DNA Polymerase Scaffold," Angewandte Chemie International Edition, 45: 7633-7635 (2006).
Ma et al., "RNA Template-dependent 5' Nuclease Activity of *Thermus aquaticus* and *Thermus thermophilus* DNA Polymerases," The Journal of Biological Chemistry, 275: 24693-24700 (2000).

(Continued)

*Primary Examiner* — Samuel Woolwine
*Assistant Examiner* — Danna Bicknell
(74) *Attorney, Agent, or Firm* — Morgan, Lewis & Bockius LLP

(57) ABSTRACT

Disclosed is a method of amplifying a polynucleotide, comprising:
(a) mixing primers for amplifying the polynucleotide, a polymerase, nucleotide substrates and a template polynucleotide, and
(b) amplifying the polynucleotide by polymerase reaction, wherein the polymerase has an amino acid sequence consisting of SEQ ID NO: 1 or an amino acid sequence with at least 85% sequence identity to SEQ ID NO: 1, and wherein an amino acid residue corresponding to position 653 of the amino acid sequence has been replaced with glutamic acid.

20 Claims, 8 Drawing Sheets

(56) References Cited

OTHER PUBLICATIONS

Arakawa et al., "Application of N-terminally Truncated DNA Polymerase from *Thermus thermophilus* (DeltaTth Polymerase) to DNA Sequencing and Polymerase Chain Reactions: Comparative Study of DeltaTth and Wild-Type Tth Polymerases," DNA Research, 3: 87-92 (1996).

Longo et al., "Use of uracil DNA glycosylase to control carry-over contamination in polymerase chain reactions," Gene, 93: 125-128 (1990).

Office Action issued in corresponding European Patent Application No. 12176175.3 dated Aug. 8, 2013.

Office Action issued in corresponding European Patent Application No. 12176175.3 dated Feb. 5, 2014.

* cited by examiner

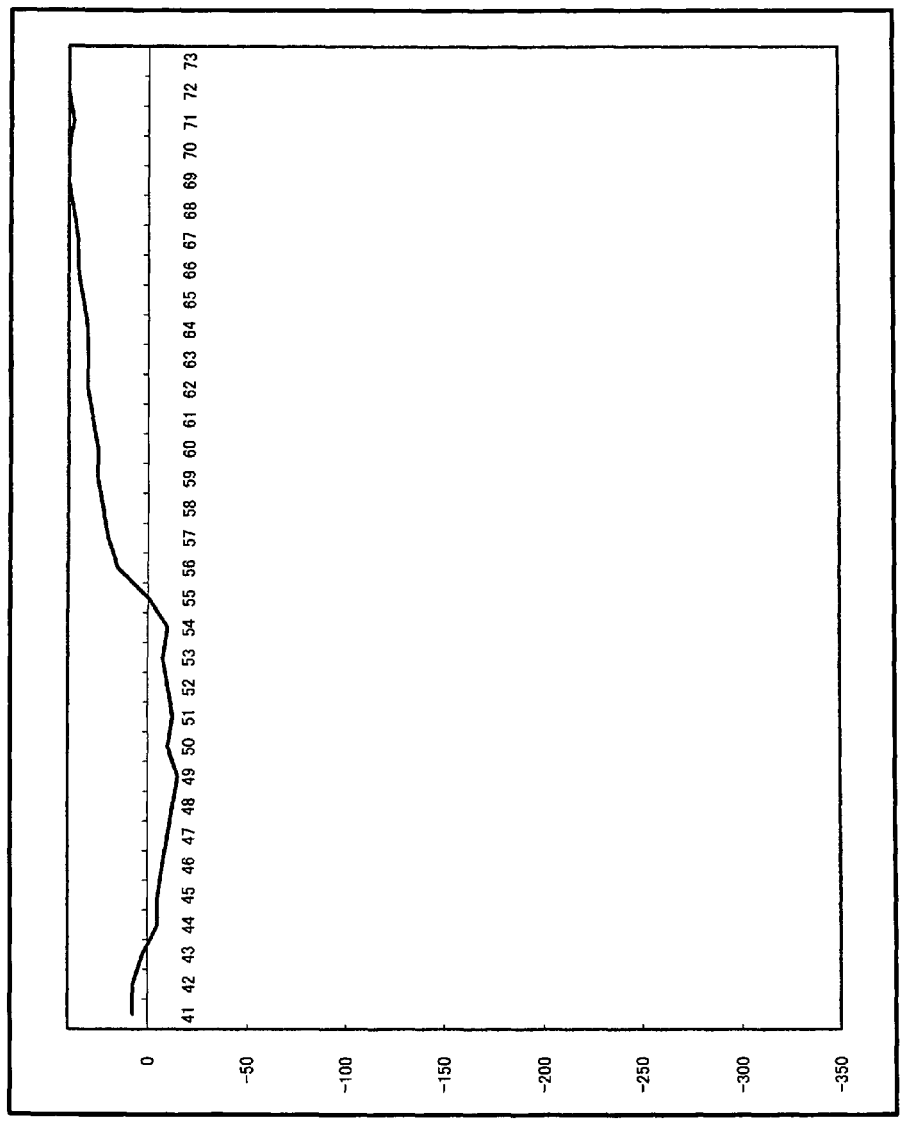

SEQUENCE LISTING

```
<160> NUMBER OF SEQ ID NOS: 10

<210> SEQ ID NO 1
<211> LENGTH: 834
<212> TYPE: PRT
<213> ORGANISM: Thermus thermophilus
```

-continued

<400> SEQUENCE: 1

Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
        115                 120                 125

Lys Ala Glu Lys Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Arg
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Leu Leu Lys Asn Leu Asp Arg
    210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
                245                 250                 255

Glu Val Asp Leu Ala Gln Gly Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu Ala Pro Ala Pro Leu Glu Glu Ala Pro Trp Pro Pro Pro
    290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Arg Asp Gly Arg Val His Arg
                325                 330                 335

Ala Ala Asp Pro Leu Ala Gly Leu Lys Asp Leu Lys Glu Val Arg Gly
            340                 345                 350

Leu Leu Ala Lys Asp Leu Ala Val Leu Ala Ser Arg Glu Gly Leu Asp
        355                 360                 365

Leu Val Pro Gly Asp Asp Pro Met Leu Leu Ala Tyr Leu Leu Asp Pro
    370                 375                 380

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ser Glu Arg Leu His Arg
                405                 410                 415

```
Asn Leu Leu Lys Arg Leu Glu Gly Glu Lys Leu Leu Trp Leu Tyr
                420                 425                 430

His Glu Val Glu Lys Pro Leu Ser Arg Val Leu Ala His Met Glu Ala
            435                 440                 445

Thr Gly Val Arg Arg Asp Val Ala Tyr Leu Gln Ala Leu Ser Leu Glu
        450                 455                 460

Leu Ala Glu Glu Ile Arg Arg Leu Glu Glu Val Phe Arg Leu Ala
465                 470                 475                 480

Gly His Pro Phe Asn Leu Asn Ser Arg Asp Gln Leu Glu Arg Val Leu
                485                 490                 495

Phe Asp Glu Leu Arg Leu Pro Ala Leu Gly Lys Thr Gln Lys Thr Gly
            500                 505                 510

Lys Arg Ser Thr Ser Ala Ala Val Leu Glu Ala Leu Arg Glu Ala His
            515                 520                 525

Pro Ile Val Glu Lys Ile Leu Gln His Arg Glu Leu Thr Lys Leu Lys
        530                 535                 540

Asn Thr Tyr Val Asp Pro Leu Pro Ser Leu Val His Pro Arg Thr Gly
545                 550                 555                 560

Arg Leu His Thr Arg Phe Asn Gln Thr Ala Thr Ala Thr Gly Arg Leu
                565                 570                 575

Ser Ser Ser Asp Pro Asn Leu Gln Asn Ile Pro Val Arg Thr Pro Leu
            580                 585                 590

Gly Gln Arg Ile Arg Arg Ala Phe Val Ala Glu Ala Gly Trp Ala Leu
                595                 600                 605

Val Ala Leu Asp Tyr Ser Gln Ile Glu Leu Arg Val Leu Ala His Leu
610                 615                 620

Ser Gly Asp Glu Asn Leu Ile Arg Val Phe Gln Glu Gly Lys Asp Ile
625                 630                 635                 640

His Thr Gln Thr Ala Ser Trp Met Phe Gly Val Pro Pro Glu Ala Val
                645                 650                 655

Asp Pro Leu Met Arg Arg Ala Ala Lys Thr Val Asn Phe Gly Val Leu
            660                 665                 670

Tyr Gly Met Ser Ala His Arg Leu Ser Gln Glu Leu Ala Ile Pro Tyr
        675                 680                 685

Glu Glu Ala Val Ala Phe Ile Glu Arg Tyr Phe Gln Ser Phe Pro Lys
690                 695                 700

Val Arg Ala Trp Ile Glu Lys Thr Leu Glu Glu Gly Arg Lys Arg Gly
705                 710                 715                 720

Tyr Val Glu Thr Leu Phe Gly Arg Arg Arg Tyr Val Pro Asp Leu Asn
                725                 730                 735

Ala Arg Val Lys Ser Val Arg Glu Ala Ala Glu Arg Met Ala Phe Asn
            740                 745                 750

Met Pro Val Gln Gly Thr Ala Ala Asp Leu Met Lys Leu Ala Met Val
        755                 760                 765

Lys Leu Phe Pro Arg Leu Arg Glu Met Gly Ala Arg Met Leu Leu Gln
770                 775                 780

Val His Asp Glu Leu Leu Leu Glu Ala Pro Gln Ala Arg Ala Glu Glu
785                 790                 795                 800

Val Ala Ala Leu Ala Lys Glu Ala Met Glu Lys Ala Tyr Pro Leu Ala
                805                 810                 815

Val Pro Leu Glu Val Glu Val Gly Met Gly Glu Asp Trp Leu Ser Ala
            820                 825                 830

Lys Gly
```

```
<210> SEQ ID NO 2
<211> LENGTH: 14
<212> TYPE: DNA
<213> ORGANISM: Artificial Sequence
<220> FEATURE:
<223> OTHER INFORMATION: probe

<400> SEQUENCE: 2
ccgtcaatgg tcac                                                         14

<210> SEQ ID NO 3
<211> LENGTH: 29
<212> TYPE: DNA
<213> ORGANISM: Artificial Sequence
<220> FEATURE:
<223> OTHER INFORMATION: primer

<400> SEQUENCE: 3
tccagttaac aaatacagca ctggcatgg                                         29

<210> SEQ ID NO 4
<211> LENGTH: 36
<212> TYPE: DNA
<213> ORGANISM: Artificial Sequence
<220> FEATURE:
<223> OTHER INFORMATION: primer

<400> SEQUENCE: 4
tgataattag tgagttgggt gatacataca caaggg                                 36

<210> SEQ ID NO 5
<211> LENGTH: 20
<212> TYPE: DNA
<213> ORGANISM: Artificial Sequence
<220> FEATURE:
<223> OTHER INFORMATION: probe

<400> SEQUENCE: 5
cagaatatac atccrgtcac                                                   20

<210> SEQ ID NO 6
<211> LENGTH: 23
<212> TYPE: DNA
<213> ORGANISM: Artificial Sequence
<220> FEATURE:
<223> OTHER INFORMATION: primer

<400> SEQUENCE: 6
gtgctataaa caccagccty cca                                               23

<210> SEQ ID NO 7
<211> LENGTH: 24
<212> TYPE: DNA
<213> ORGANISM: Artificial Sequence
<220> FEATURE:
<223> OTHER INFORMATION: primer

<400> SEQUENCE: 7
cgggatattc cttaatcctg trgc                                              24

<210> SEQ ID NO 8
<211> LENGTH: 17
<212> TYPE: DNA
<213> ORGANISM: Artificial Sequence
<220> FEATURE:
<223> OTHER INFORMATION: probe
```

```
<400> SEQUENCE: 8
ggctgcacgc tactcac                                                17

<210> SEQ ID NO 9
<211> LENGTH: 28
<212> TYPE: DNA
<213> ORGANISM: Artificial Sequence
<220> FEATURE:
<223> OTHER INFORMATION: primer

<400> SEQUENCE: 9
gttatcccag aaggctttgc aggcttca                                    28

<210> SEQ ID NO 10
<211> LENGTH: 26
<212> TYPE: DNA
<213> ORGANISM: Artificial Sequence
<220> FEATURE:
<223> OTHER INFORMATION: primer

<400> SEQUENCE: 10
gccgactgag ccctgggagg taggta                                      26
```

METHOD AND KIT FOR AMPLIFYING AND DETECTING POLYNUCLEOTIDE USING A MODIFIED TTH POLYMERASE

CROSS-REFERENCE TO RELATED APPLICATION

This application claims priority from Japanese Patent Application No. JP2011-153455 filed on Jul. 12, 2011. The entire subject matter of the Japanese Patent Application is incorporated herein by reference in its entirety.

SEQUENCE LISTING SUBMISSION VIA EFS-WEB

A computer readable text file, entitled "SequenceListing.txt," created on or about Jul. 4, 2012 with a file size of about 9 kb contains the sequence listing for this application and is hereby incorporated by reference in its entirety.

TECHNICAL FIELD

The present invention relates to a method and a kit for amplifying a polynucleotide and detecting the amplified polynucleotide.

BACKGROUND ART

In order to amplify DNA by using PCR, a pair of nucleotide primer, the region between which is a target polynucleotide; a polymerase; and nucleotide triphosphates that are substrates for the polymerase and form the polynucleotide after the amplification, are needed. After the amplification, the target polynucleotide may be detected by any method, for example, by using a specific nucleic acid probe that has a sequence complementary to the target sequence.

In addition, there is a method of amplifying cDNA by using reverse transcription (RT) PCR. In this case, a polymerase having a reverse transcriptional activity may be used.

Moreover, uracil DNA glycosylase (UNG) method, wherein deoxyuridine triphosphate, an unnatural type nucleotide triphosphate, is used to prevent amplification product contamination, is also known (JP3,392,863B).

However, such conventional techniques generally had problems that (1) the number of polymerases that have a reverse transcriptional activity is limited; (2) contamination may not be prevented, because general polymerases often do not incorporate deoxyuridine triphosphate which is a substrate during amplification; and therefore the degradation of uracil N-glycosylase in UNG method cannot be attained; and (3) the higher amplification speed is preferred.

Thus, a method of rapidly amplifying and detecting a long chain target polynucleotide, wherein reverse transcription can be carried out; and deoxyuridine triphosphate can be used, has been demanded.

SUMMARY OF THE INVENTION

An object of the present invention is to provide a method of rapidly amplifying and detecting a long chain target polynucleotide, wherein reverse transcription can be carried out; deoxyuridine triphosphate can be used; and the degradation of the synthesized polynucleotide chains can be prevented.

The present inventors have discovered that Tth polymerase wherein proline at position 653 in SEQ ID NO:1 has been replaced with glutamic acid has a reverse transcriptional activity and can incorporate deoxyuridine triphosphate, and, in addition, that its 5'→3' exonuclease activity can be reduced by deleting the amino acids at positions 1 to 77 or the amino acids at positions 1 to 291 in SEQ ID NO:1, thereby completing the present invention.

That is, the present invention is as follows.
(1) A method of amplifying a polynucleotide, comprising:
   (a) mixing primers for amplifying the polynucloetide, a polymerase, nucleotide substrates and a template polynucleotide, and
   (b) amplifying the polynucleotide by polymerase reaction, wherein the polymerase has an amino acid sequence consisting of SEQ ID NO:1 or an amino acid sequence with at least 85%, 86%, 87%, 88%, 89%, 90%, 91%, 92%, 93%, 94%, 95%, 96%, 97%, 98% or 99% sequence identity to SEQ ID NO:1, wherein an amino acid residue corresponding to position 653 of the amino acid sequence has been replaced with glutamic acid.
(2) A method of amplifying and detecting a polynucleotide, comprising:
   (a) mixing primers for amplifying the polynucleotide, a polymerase, nucleotide substrates, a probe for detecting the amplified polynucleotide and a template polynucleotide,
   (b) amplifying the polynucleotide by polymerase reaction, and
   (c) detecting the polynucleotide by using the probe, wherein the polymerase has an amino acid sequence consisting of SEQ ID NO:1 or an amino acid sequence with at least 85%, 86%, 87%, 88%, 89%, 90%, 91%, 92%, 93%, 94%, 95%, 96%, 97%, 98% or 99% sequence identity to SEQ ID NO:1, and wherein an amino acid residue corresponding to position 653 of the amino acid sequence has been replaced with glutamic acid.
(3) The method according to (2), wherein the detecting step (c) is carried out by detection of PCR product accumulated during the amplification reaction or by melting curve analysis.
(4) The method according to (1), wherein the polynucleotide is DNA or RNA.
(5) The method according to (4), wherein the amplifying step (b) is carried out by PCR or RT-PCR.
(6) The method according to (1), wherein the nucleotide substrates comprise deoxyuridine triphosphate.
(7) The method according to (1), wherein the polymerase is a modified Tth polymerase wherein the amino acids at the N-terminal side have been deleted to delete or reduce the 5'→3' exonuclease activity.
(8) The method according to (7), wherein the polymerase is a modified Tth polymerase wherein the amino acids at positions 1 to 77 of SEQ ID NO:1 have been deleted.
(9) The method according to (7), wherein the polymerase is a modified Tth polymerase wherein the amino acids at positions 1 to 291 of SEQ ID NO:1 have been deleted.
(10) The method according to (1), wherein in the step (b), the polynucleotide is amplified at not less than 20 nucleotides/sec.
(11) The method according to (10), wherein the polynucleotide amplified in the step (b) has a nucleotide length of not less than 600 nucleotides.
(12) A kit for amplifying a polynucleotide, comprising primers for amplifying the polynucleotide, a polymerase, and nucleotide substrates,
   wherein the polymerase has an amino acid sequence consisting of SEQ ID NO:1 or an amino acid sequence with at least 85%, 86%, 87%, 88%, 89%, 90%, 91%, 92%, 93%, 94%, 95%, 96%, 97%, 98% or 99% sequence identity to SEQ ID NO:1, and wherein an amino acid residue corresponding to position 653 of the amino acid sequence has been replaced with glutamic acid.

(13) A kit for amplifying and detecting a polynucleotide, comprising primers for amplifying the polynucleotide, a polymerase, nucleotide substrates, and a probe for detecting the amplified polynucleotide,
wherein the polymerase has an amino acid sequence consisting of SEQ ID NO:1 or an amino acid sequence with at least 85%, 86%, 87%, 88%, 89%, 90%, 91%, 92%, 93%, 94%, 95%, 96%, 97%, 98% or 99% sequence identity to SEQ ID NO:1, and wherein an amino acid residue corresponding to position 653 of the amino acid sequence has been replaced with glutamic acid.

(14) The kit according to (12), wherein the nucleotide substrates comprise deoxyuridine triphosphate.

The polymerases used in the present invention have a reverse transcriptional activity, and therefore both DNA and RNA nucleic acids can be amplified by using such polymerases.

The polymerases used in the present invention can incorporate deoxyuridine triphosphate, and therefore amplification product contamination can be prevented by using such polymerases and, for example carrying out UNG method.

The method of the present invention can allow amplification of a polynucleotide under a condition of not less than 20 nucleotides/sec, and can improve amplification speed. The method of the present invention is very useful especially in amplifying a long chain having a nucleotide length of not less than 600 nucleotides.

In addition, the 5'→3' exonuclease activity of the polymerases to be used in the present invention may be deleted or reduced by deleting the amino acids at positions 1 to 771 to 77 or the amino acids at positions 1 to 291 in SEQ ID NO:1. This will prevent degradation of the nucleic acid probe in the reaction solution in the method of the present invention, and thereby can allow detection of the probe during amplification and melting curve analysis after amplification.

DETAILED DESCRIPTION OF THE INVENTION

Figure 1A:
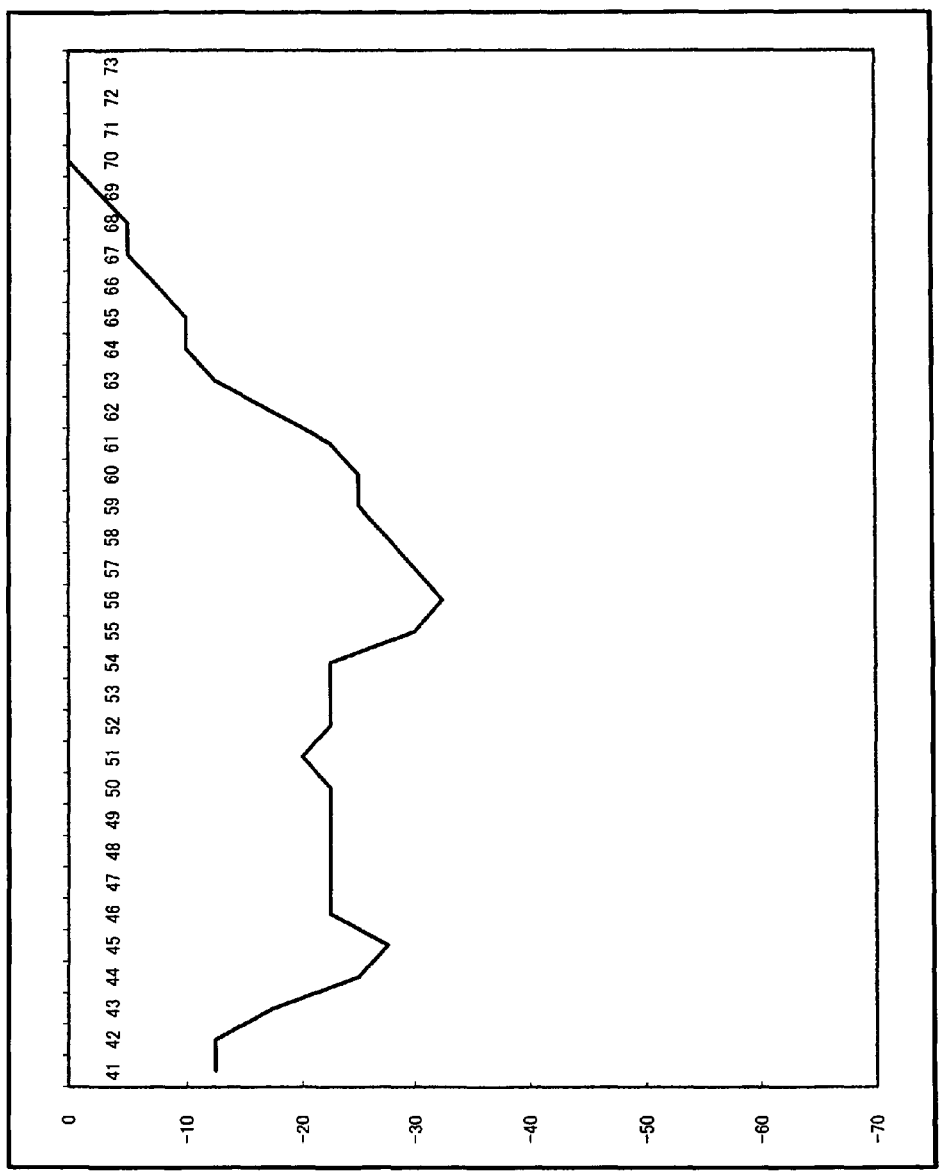
FIG. 1 shows the change in Tm analysis for a NAT2 gene in the amount of the change in the fluorescence intensity per unit time (−d(Amount of Increase in Fluorescence Intensity)/t) in case where dNTPmix as the substrates and Tth were used (FIG. 1A), in case where dNTPmix as the substrates and modified Tth were used (FIG. 1B), in case where dAUGCmix as the substrates and Tth were used (FIG. 1C), and in case where dAUGCmix as the substrates and modified Tth were used (FIG. 1D), in Example 1. The ordinate represents the amount of the change in the fluorescence intensity per unit time (−d(Amount of Increase in Fluorescence Intensity)/t), and the abscissa represents the temperature (° C.).

<1> Amplification and Detection Method of Present Invention

The method of the present invention is a method of amplifying a polynucleotide, comprising:

(a) mixing primers for amplifying the polynucleotide, a polymerase, nucleotide substrates and a template polynucleotide, and (b) amplifying the polynucleotide by polymerase reaction, wherein the polymerase has an amino acid sequence consisting of SEQ ID NO:1 or an amino acid sequence with at least 85%, 86%, 87%, 88%, 89%, 90%, 91%, 92%, 93%, 94%, 95%, 96%, 97%, 98% or 99% sequence identity to SEQ ID NO:1, and wherein an amino acid residue corresponding to position 653 of the amino acid sequence has been replaced with glutamic acid.

The method of the present invention may also comprise, after the above-described steps (a) and (b), the step (c) of detecting the polynucleotide by using a probe.

In other words, the method of the present invention is a method of amplifying and detecting a polynucleotide, comprising:

(a) mixing primers for amplifying the polynucleotide, a polymerase, nucleotide substrates, a probe for detecting the amplified polynucleotide and a template polynucleotide, (b) amplifying the polynucleotide by polymerase reaction, and (c) detecting the polynucleotide by using the probe, wherein the polymerase has an amino acid sequence consisting of SEQ ID NO:1 or an amino acid sequence with at least 85%, 86%, 87%, 88%, 89%, 90%, 91%, 92%, 93%, 94%, 95%, 96%, 97%, 98% or 99% sequence identity to SEQ ID NO:1, and wherein an amino acid residue corresponding to position 653 of the amino acid sequence has been replaced with glutamic acid.

The detecting step (c) may be carried out by detection of PCR product accumulated during the amplification reaction or by melting curve analysis.

The method of the present invention will be carried out by the step (a) and the step (b), and the optional step (c), but the steps (a) to (c) may be carried out in the same manner as conventional methods except that the specified polymerases are used as a polymerase.

The polymerases used in the present invention are characterized in that proline at position 653 in the amino acid sequence of SEQ ID NO:1, which is a polymerase from thermophilic bacterium *Thermus thermophilus* HB8 (i.e., a Tth polymerase), has been replaced with glutamic acid.

The modified Tth polymerase used in the present invention, wherein proline at position 653 in SEQ ID NO:1 (the amino acid sequence around position 653 in SEQ ID NO:1 is represented by—Phe Gly Val Pro <u>Pro</u> Glu Ala Val Asp—, wherein the underlined amino acid indicates proline at position 653) has been replaced with glutamic acid (the amino acid sequence around position 653 in SEQ ID NO:1 is represented by—Phe Gly Val Pro <u>Glu</u> Glu Ala Val Asp—, wherein the underlined amino acid indicates a glutamic acid at the substituted position 653), has an increased polymerase activity compared to a wild type Tth polymerase wherein proline at position 653 is not replaced with glutamic acid.

The polymerases to be used in the present invention may be a polymerase wherein proline at position 653 in SEQ ID NO:1 has been replaced with glutamic acid; in addition to this, the amino acids at positions 1 to 77 or the amino acids at positions 1 to 291 in SEQ ID NO:1 have been deleted; and therefore its 5'→3' exonuclease activity has been deleted or reduced.

The nucleotide sequence encoding a wild type polymerase to be used in the present invention includes, for example, the nucleotide sequence registered as GenBank Acc. No. D28878.

In the present invention, the polymerase has an amino acid sequence consisting of SEQ ID NO:1 or an amino acid sequence with at least 85%, 86%, 87%, 88%, 89%, 90%, 91%, 92%, 93%, 94%, 95%, 96%, 97%, 98% or 99% sequence identity to SEQ ID NO:1.

As used herein, "sequence identity" is a measure of the identity of nucleotide sequences or amino acid sequences compared to a reference nucleotide or amino acid sequence. In general, the sequences are aligned so that the highest order match is obtained. "Sequence identity" per se has an art-recognized meaning and can be calculated using published techniques (see Computer Analysis of Sequence Data, Part I, Griffin, ed. Humana Press (1994)). Computer software may also contain methods and algorithms that calculate sequence identity. Examples of computer software methods to determine identity and similarity between two sequences include, but are not limited to, BLASTP, ExPASy, BLASTN, FASTA and FASTDB.

In one embodiment of the present invention, the algorithm used to determine identity between two or more polypeptides is BLASTP. In another embodiment of the present invention, the algorithm used to determine identity between two or more polypeptides is FASTDB. In a FASTDB sequence alignment, the query and reference sequences are amino acid sequences. The result of sequence alignment is in percent sequence identity. In one embodiment, parameters that may be used in a FASTDB alignment of amino acid sequences to calculate percent identity include, but are not limited to: Matrix=PAM, k-tuple=2, Mismatch Penalty=1, Joining Penalty=20, Randomization Group Length=0, Cutoff Score=1, Gap Penalty=5, Gap Size Penalty 0.05, Window Size=500 or the length of the subject amino sequence, whichever is shorter.

As used herein, the terms "corresponds to" and "corresponding to" as they relate to sequence alignment, are intended to mean enumerated positions within the reference polypeptide, e.g. SEQ ID NO:1, and those positions in the modified Tth polymerase polypeptide that align with the positions on the reference polypeptide. Thus, when the amino acid sequence of a subject Tth polymerase polypeptide is aligned with the amino acid sequence of a reference Tth polymerase polypeptide, e.g. SEQ ID NO:1, the amino acids in the subject sequence that "correspond to" certain enumerated positions of the reference sequence are those that align with these positions of the reference sequence, e.g., SEQ ID NO:1, but are not necessarily in these exact numerical positions of the reference sequence. Methods for aligning sequences for determining corresponding amino acids between sequences are described herein.

In the method of the present invention, a Tth polymerase as described above is used, but the polymerase may be, for example, a protein having an amino acid sequence wherein 1 or more, 2 to 10, or 2 to 5 amino acid residues have been substituted, deleted, inserted or added in the amino acid sequence of SEQ ID NO:1 or in the amino acid sequence wherein the amino acids at positions 1 to 77 or the amino acids at positions 1 to 291 in SEQ ID NO:1 have been deleted, as long as proline at position 653 in SEQ ID NO:1 has been replaced with glutamic acid and the polymerase activity is not lost.

The positions of the amino acid substitution mutations as described above indicate positions in the amino acid sequence of the Tth polymerase of SEQ ID NO:1. However, in cases of homologues or variants of the Tth polymerase, which have an amino acid sequence wherein one or more amino acid residues in the amino acid sequence of SEQ ID NO:1 have been substituted, deleted, inserted or added other than the above-described specified mutation(s), the positions of the amino acid substitution mutations as described above mean positions corresponding to the above-described amino acid substitution positions in the amino acid sequence alignment of the homologue or variant with SEQ ID NO:1. For example, in case of a conservative variant of the Tth polymerase, wherein one amino acid residue in the region between position 1 and position 652 has been deleted, position 653 as described above means position 652 of this variant. As another example, in case of a conservative variant of the Tth polymerase, wherein the amino acid residues at positions 1 to 77 have been deleted, position 653 as described above means position 576 of this variant. As yet another example, in case of a conservative variant of the Tth polymerase, wherein the amino acid residues at positions 1 to 291 have been deleted, position 653 as described above means position 362 of this variant.

Similarly, the Tth polymerase of the present invention may be a protein having an amino acid identity of at least 80%, 85%, 90%, or 95% to the amino acid sequence of SEQ ID NO:1 or the amino acid sequence wherein the amino acids at positions 1 to 77 or the amino acids at positions 1 to 291 in SEQ ID NO:1 have been deleted, as long as proline at position 653 in SEQ ID NO:1 (the amino acid sequence around position 653 in SEQ ID NO:1 is represented by—Phe Gly Val Pro Pro Glu Ala Val Asp—, wherein the underlined amino acid indicates proline at position 653) has been replaced with glutamic acid (the amino acid sequence around position 653 in SEQ ID NO:1 is represented by—Phe Gly Val Pro Glu Glu Ala Val Asp—, wherein the underlined amino acid indicates a glutamic acid at the substituted position 653); and the polymerase activity is not lost.

Furthermore, the polymerases used in the present invention have a reverse transcriptional activity. Therefore, by using such a polymerase, both DNA and RNA can be amplified using them as a template, and RT-PCR can be carried out. When a reverse transcriptase and a DNA polymerase are used in combination, it is often necessary to adjust the reactions of these enzymes appropriately. However, even in case of using a reverse transcriptase and a DNA polymerase in combination, the polymerases used in the present invention can be used without careful adjustment. In addition, in cases where the polymerases used in the present invention are used, reverse transcription reaction and PCR can be carried out using a single enzyme, and therefore two-step operation, wherein reverse transcription reaction and PCR are carried out in separate tubes, is not needed; and RT-PCR can be carried out in one-step operation.

The primers used in the present invention are not particularly limited and may be designed using a conventional method, as long as they are designed such that a desired region can be amplified.

For example, a combination of the deoxyribonucleotides to be used in the present invention is a combination of deoxyadenosine triphosphate (dATP), deoxyguanosine triphosphate (dGTP), deoxycytidine triphosphate (dCTP), and thymidine triphosphate (dTTP), or a combination of deoxyadenosine triphosphate (dATP), deoxyguanosine triphosphate (dGTP), deoxycytidine triphosphate (dCTP), and deoxyuridine triphosphate (dUTP), but ddNTPs, modified nucleotides and so on may also be used.

Since the polymerases of the present invention can incorporate deoxyuridine triphosphate, UNG method may also be carried out in the method of the present invention to prevent amplification product contamination.

As the nucleic acid probe for detecting the amplified polynucleotide to be used in the method of the present invention, for example, a quenching probe labeled with a fluorescent dye in its terminal region, as described in JP2001-286300A and JP2002-119291A, may be used. For example, the nucleic acid probe is a probe wherein the fluorescence of its fluorescent dye at the time when the probe is hybridizing to its target sequence is decreased or increased, as compared to the fluorescence at the time when the probe is not hybridizing to its target sequence. For example, the nucleic acid probe in the present invention is a quenching probe wherein the fluorescence of its fluorescent dye is emitted when the probe is not hybridizing; and the fluorescence of its fluorescent dye is quenched when the probe is hybridizing.

Samples containing a polynucleotide to be a template in carrying out the polynucleotide amplification are not particularly limited, as long as the sample contains a polynucleotide. Examples of the sample include samples that are derived from or can be derived from any biological sources, such as blood, a suspension of oral mucosa, somatic cells of a nail, a hair and so on, germ cells, milk, ascitic fluid, a paraffin-embedded tissue, gastric juice, a gastric washing, peritoneal fluid, amniotic fluid, and a cell culture. As the polynucleotide to be used as a template, a polynucleotide obtained from such a source may be directly used without any treatment, or may be used after pretreatment to change the nature of the sample.

In general, the polynucleotide in the sample may be DNA or RNA, and may be either a single strand or a double strand.

The step (a) in the method of the present invention may be carried out by adding to a reaction solution the polymerase, the primers, and the nucleotides that are substrates, and optionally the nucleic acid probe, together with a sample containing a polynucleotide, in predetermined amounts, and mixing them.

The step (b) in the method of the present invention may be carried out by a conventional polynucleotide amplification method, such as PCR or RT-PCR. A target gene may be amplified by ICAN method using DNA-RNA chimeric primers, RNase H, and the above-described polymerase. Alternatively, a target gene may also be amplified by LAMP method using inner primers, outer primers, loop primers, and the above-described polymerase.

In case where detection of the amplified polynucleotide is carried out, the amplification may be performed in the presence of a nucleic acid probe. In other words, in case where the step (c) is carried out, the probe may be added in the step (a).

In the step (b) in the method of the present invention, a polynucleotide may be amplified under a condition of not less than 20 nucleotides/sec by using the polymerases of the present invention.

For example, the step (c) in the method of the present invention is a step wherein melting curve analysis is performed using the above-mentioned probe to detect the amplified region. The method of the present invention may be carried out according to conventional methods of polynucleotide amplification and melting curve analysis (Tm analysis), except that the polymerase of the present invention is used. For example, the step (c) is a step wherein a nucleic acid probe labeled with a fluorescent dye is used for the amplified polynucleotide; melting curve analysis is carried out by measuring the fluorescence of the fluorescent dye; and the amplified region is detected based on the results of the melting curve analysis. The step (c) in the method of the present invention may be carried out according to a conventional method of melting curve analysis (Tm analysis).

Alternatively, the step (c) in the method of the present invention may be carried out by detection of PCR product accumulated during the amplification reaction. More specifically, the step (c) may be carried out by quantitative PCR, wherein a system, in which the fluorescence is changed depending on the amount of the amplification product, is used; quantification of the amplification product in PCR is carried out in real time by measuring the fluorescence; and, based on the results, DNA in the sample is quantified, and thus may be carried out according to a known method. Examples of such a method include a method wherein a fluorescently labeled probe, that can hybridize to the amplification product, is used. As the fluorescently labeled probe, the above-described probe may be used. The step (c) in the method of the present invention may be carried out according to a conventional real-time PCR method by measuring the fluorescence of a fluorescent dye, except that the above-described probe is used. Adjusting the reaction conditions of the amplification and so on according to the probe to be used will be easily attained by those having skill in the art.

In the method of the present invention, the step (c) may be carried out simultaneously with the step (b).

In the step (c) in the method of the present invention, only analysis of the Tm of the probe after amplification of a polynucleotide, or detection of the amount of the PCR product as a fluorescence value is performed, and, therefore it is not necessary to handle the amplification product after completion of the reaction. Thus, there is no concern for contamination by the amplification product. In addition, the detection can be performed in the same apparatus as the apparatus required in the amplification, and therefore it is not necessary even to transfer a vessel.

<2> Kit of Present Invention

The kit of the present invention is a kit for using in the detection method of the present invention.

In other words, the kit of the present invention is a kit for amplifying and detecting a polynucleotide, comprising primers for amplifying the polynucleotide, a polymerase, nucleotide substrates, and a probe for detecting the amplified polynucleotide, wherein the polymerase has an amino acid sequence consisting of SEQ ID NO:1 or an amino acid sequence with at least 85%, 86%, 87%, 88%, 89%, 90%, 91%, 92%, 93%, 94%, 95%, 96%, 97%, 98% or 99% sequence identity to SEQ ID NO:1, and wherein an amino acid residue corresponding to position 653 of the amino acid sequence has been replaced with glutamic acid.

The kit of the present invention may also be used only for the purpose of amplifying a polynucleotide.

In other words, the kit of the present invention is a kit for amplifying a polynucleotide, comprising primers for amplifying the polynucleotide, a polymerase, and nucleotide substrates, wherein the polymerase has an amino acid sequence consisting of SEQ ID NO:1 or an amino acid sequence with at least 85%, 86%, 87%, 88%, 89%, 90%, 91%, 92%, 93%, 94%, 95%, 96%, 97%, 98% or 99% sequence identity to SEQ ID NO:1, and wherein an amino acid residue corresponding to position 653 of the amino acid sequence has been replaced with glutamic acid.

The primers, the polymerase, the nucleotides that are substrates, and the probe are as described above in relation to the method of the present invention. In the kit of the present invention, for example, the nucleotides that are substrates, comprise deoxyuridine triphosphate.

In addition to the primers, the polymerase, the nucleotides that are substrates, and the probe, the kit of the present invention may further contain reagents that are required for carrying out the polynucleotide amplification in the detection method of the present invention.

In the kit of the present invention, the primers, the polymerase, the nucleotides that are substrates, the probe and other reagents may be independently accommodated, or some of them may be accommodated as a mixture.

EXAMPLES

The present invention will now be described concretely by way of Examples.

Example 1

Case of Detecting NAT2 Gene

So as to make it possible to amplify a 640 by site containing NAT2*5 which is an N-acetyltransferase 2 (NAT2) gene, primers and a probe shown in Table 1 were used. Such primers and a probe are described in WO 2008/066161.

TABLE 1

| Name | sequence (5' → 3') | mer | SEQ ID: NO |
|---|---|---|---|
| Probe | ccgtcaatggtcac-(BODIPY FL) | 14 | 2 |
| Forward Primer | tccagttaacaaatacagcactggcatgg | 29 | 3 |
| Reverse Primer | tgataattagtgagttgggtgatacatacacaaggg | 36 | 4 |

For a 25 μl reaction solution, which contained $10^3$ copies of purified human genome, and wherein components had been mixed so as to attain the concentrations of Table 2 below, PCR and Tm analysis were performed using SMART CYCLER (manufactured by Takara Bio Inc.). The conditions of PCR and Tm analysis are as shown in Table 3 below. In Tm analysis, Optics was set to Ch1.

The substrates (*1) were dNTPmix or dAUGCmix. With regard to dAUGCmix, only dUTP had a final concentration of 600 nM. The composition of dNTPmix was dATP, dCTP, dGTP and dTTP, and the composition of dAUGCmix was dATP, dCTP, dGTP and dUTP.

The enzyme (*2) was Tth or modified Tth; Tth represents a wild type Tth polymerase wherein the amino acids at positions 1 to 77 have been deleted; and modified Tth represents a mutant Tth polymerase wherein P653E mutation has been introduced and wherein the amino acids at positions 1 to 77 have been deleted. Tth was produced as a recombinant enzyme produced by *Escherichia coli*. Modified Tth was produced by introducing a mutation in a site-specific manner so that proline at position 653 was replaced with glutamic acid.

TABLE 2

| Total Amount of Reaction Solution: 25 μl | |
|---|---|
| Tris-HCl (pH 8.6) | 25 mM |
| KCl | 40 mM |
| MgCl$_2$ | 2.5 mM |
| Substrates (*1) | 200 nM |
| BSA | 0.1% |
| Probe | 100 nM |
| Forward Primer | 500 nM |
| Reverse Primer | 500 nM |
| Purified Genome | 1000 copies |
| Enzyme (*2) | 350 ng |

TABLE 3

| Conditions of PCR and Tm Analysis |
|---|
| 95° C. for 60 sec ↓ |
| (95° C. for 1 sec, 65° C. for 30 sec) × 50 ↓ |
| 95° C. for 10 sec ↓ |
| 40° C. for 60 sec ↓ |
| Tm (40° C. → 75° C., 1° C./sec) |

Figure 1B:
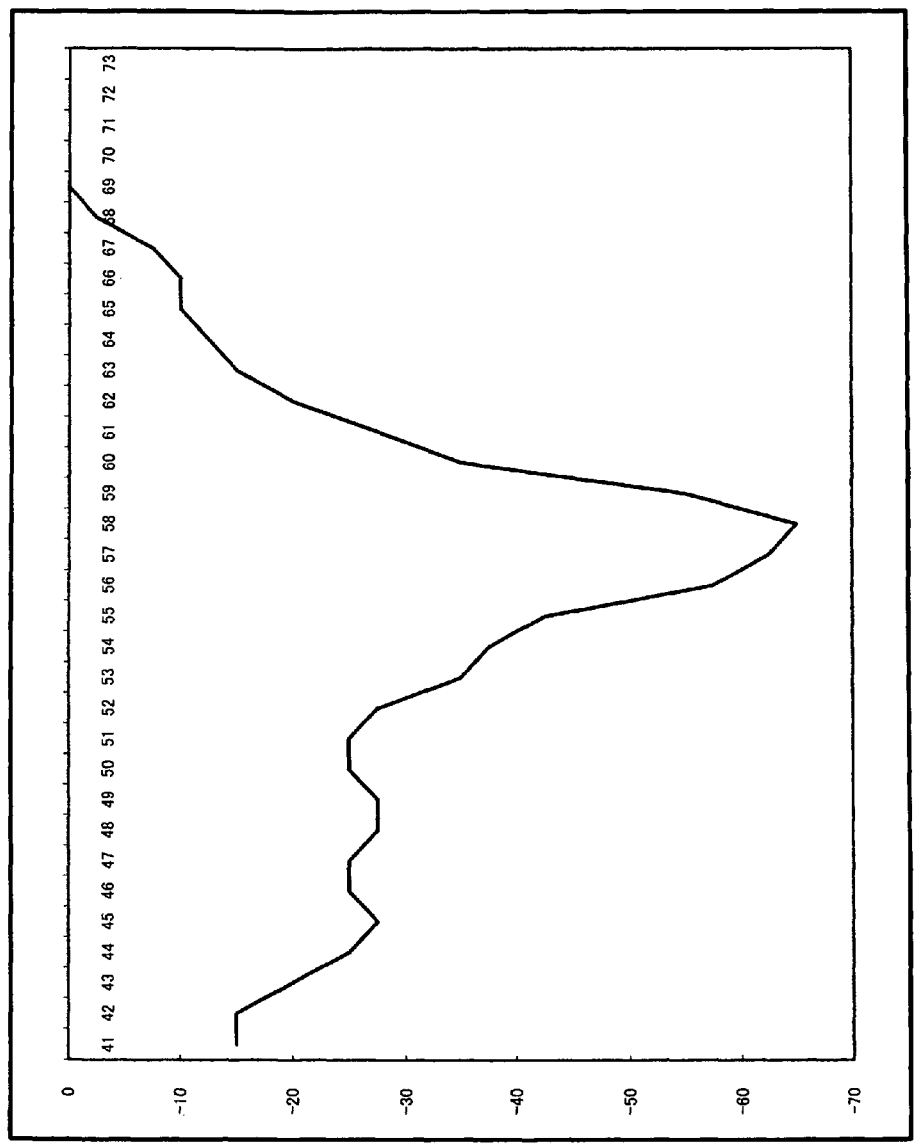

When dNTPmix was used, in case of Tth, detection by Tm analysis was not confirmed (FIG. 1A); while, in case of modified Tth, detection was attained (FIG. 1B). Since the amplification of 640 by was attained for 30 seconds, amplification of the polynucleotide at 21 bp/sec could be attained.

Figure 1C:
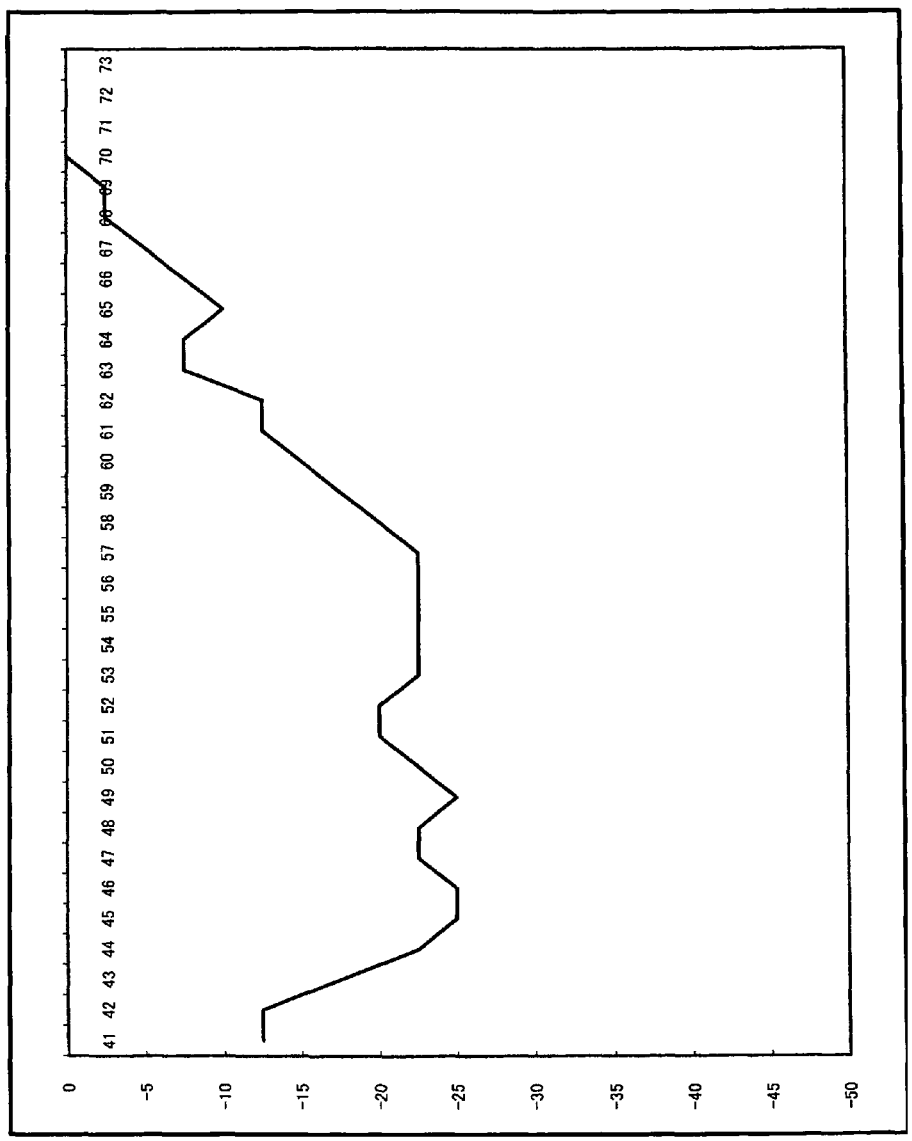
Figure 1D:
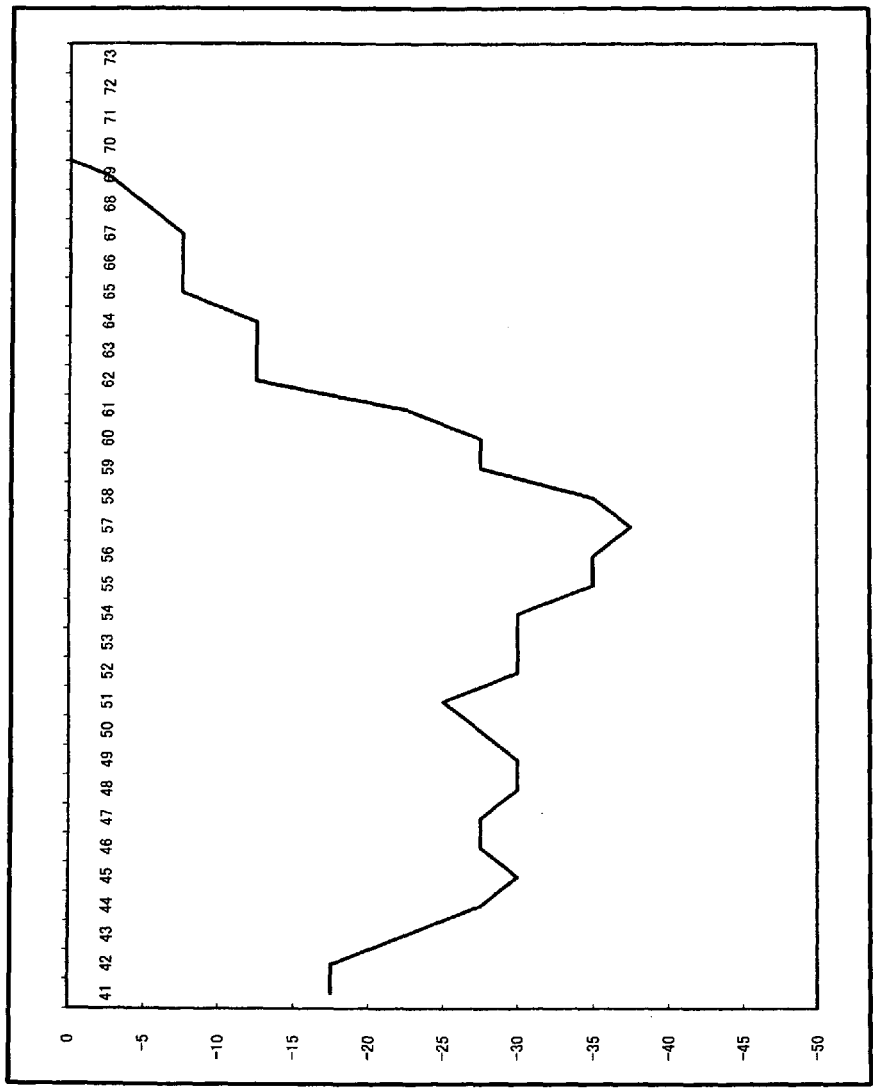

When dAUGCmix was used, in case of Tth, detection by Tm analysis was not confirmed (FIG. 1C); while, in case of modified Tth, detection was weak, but was attained (FIG. 1D).

Example 2

Case of Detecting RNA (SWlnfH1 Region))

So as to make it possible to amplify an SWlnfH1 region, primers and a probe shown in Table 4 were used. Such primers and a probe were produced with reference to the sequences described in a protocol for amplifying influenza virus issued by WHO (CDC realtime RT-PCR protocol for influenza A (H1N1), 28 Apr. 2009).

TABLE 4

| Name | sequence (5' → 3') | mer | SEQ ID: NO |
|---|---|---|---|
| Probe | CAGAATATACATCCRGTCAC-(BODIPY FL) | 20 | 5 |
| Forward Primer | GTGCTATAAACACCAGCCTYCCA | 23 | 6 |
| Reverse Primer | CGGGATATTCCTTAATCCTGTRGC | 24 | 7 |

R represents A or G.
Y represents C or T.

For a 25 μl reaction solution, which contained $10^4$ copies of RNA (an SWlnfH1 region), and wherein components had been mixed so as to attain the concentrations of Table 5 below, RT-PCR and Tm analysis were performed using SMART CYCLER (manufactured by Takara Bio Inc.). The conditions of PCR and Tm analysis are as shown below. In Tm analysis, Optics was set to Ch1.

The enzyme (*1) was Tth or modified Tth; Tth represents a wild type Tth polymerase wherein the amino acids at positions 1 to 291 have been deleted; and modified Tth represents a Tth polymerase wherein P653E mutation has been introduced and wherein the amino acids at positions 1 to 291 have been deleted.

The substrates (*2) were dAUGCmix. With regard to dAUGCmix, only dUTP had a final concentration of 600 nM. The composition of dAUGCmix was dATP, dCTP, dGTP and dUTP.

TABLE 5

| Total Amount of Reaction Solution: 25 μl | |
|---|---|
| Tris-HCl (pH 8.6) | 27 mM |
| BSA | 0.2% |
| SUPER RnaseIn. | 20 units |
| DTT | 4 mM |
| Enzyme (*1) | 350 ng |
| Substrates (*2) | 200 nM |
| Glycerol | 2.5% |
| $MgCl_2$ | 1.5 mM |
| KCl | 25 mM |
| Probe | 200 nM |
| Forward Primer | 1000 nM |
| Reverse Primer | 2000 nM |

TABLE 6

| Conditions of RT-PCR and Tm Analysis |
|---|
| 42° C. for 30 min |
| ↓ |
| 95° C. for 5 min |
| ↓ |
| (95° C. for 1 sec, 60° C. for 30 sec) × 50 |
| ↓ |
| 95° C. for 10 sec |
| ↓ |
| 40° C. for 60 sec |
| ↓ |
| Tm (40° C. → 75° C., 1° C./sec) |

Figure 2B:
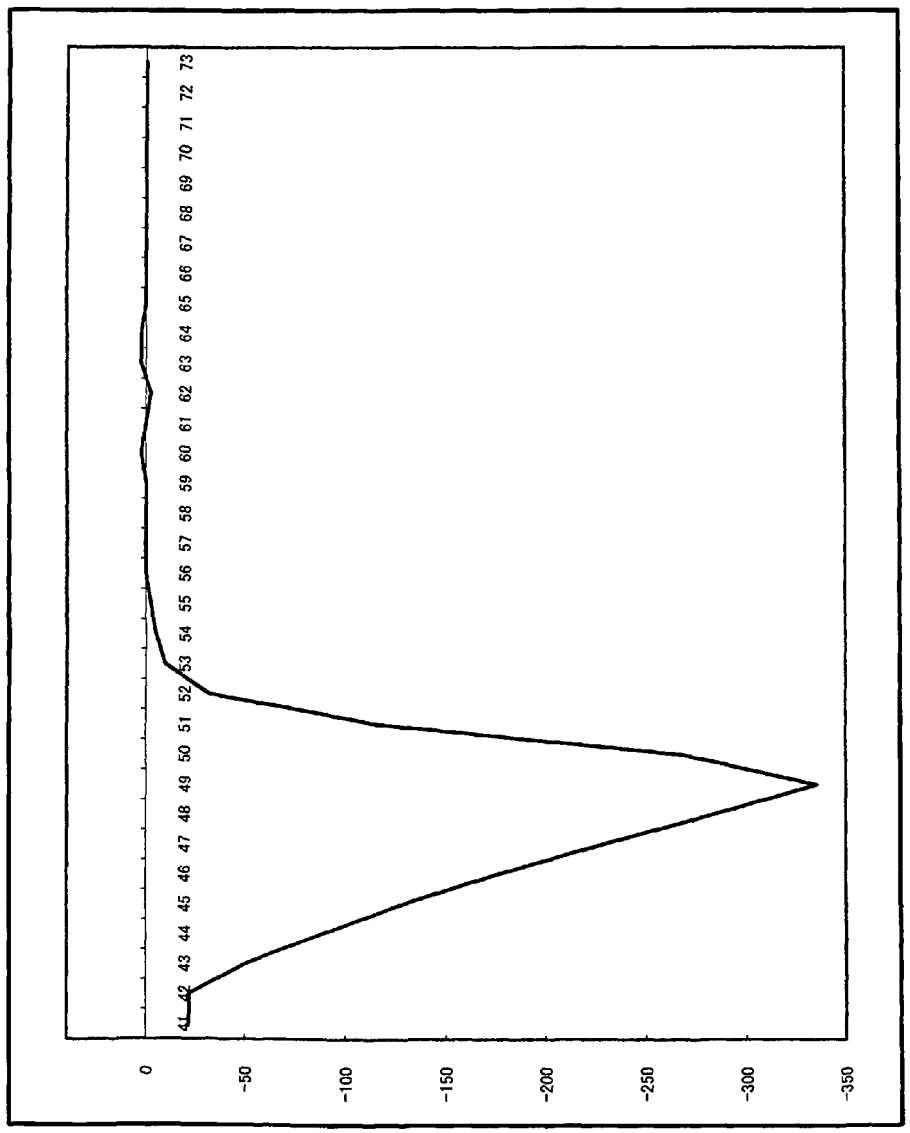
FIG. 2 shows the change in Tm analysis for RNA (an SWlnfH1 region) in the amount of the change in the fluorescence intensity per unit time (−d(Amount of Increase in Fluorescence Intensity)/t) in cases where dAUGCmix as the substrates and Tth (FIG. 2A) or modified Tth (FIG. 2B) were used, in Example 2. The ordinate represents the amount of the change in the fluorescence intensity per unit time (−d (Amount of Increase in Fluorescence Intensity)/t), and the abscissa represents the temperature (° C.).

In case of Tth, there was no detection peak after RT-PCR amplification that could be confirmed (FIG. 2A); while, in case of modified Tth, a detection peak was confirmed (FIG. 2B).

Example 3

Case of Detecting CYP2D6 Gene

So as to make it possible to amplify a 5.1 kbp site containing a CYP2D6 gene, primers and a probe shown in Table 7 were used. Such primers and a probe are described in Clinical Chemistry 46, No. 8, 2000, p.p. 1072-1077; and JP4,437,207B.

TABLE 7

| Name | sequence (5' → 3') | mer | SEQ ID: NO |
|---|---|---|---|
| Probe | ggctgcacgctactcac-(BODIPY FL) | 17 | 8 |
| Forward Primer | gttatcccagaaggctttgcaggcttca | 28 | 9 |
| Reverse Primer | gccgactgagccctgggaggtaggta | 26 | 10 |

For a 25 μl reaction solution, which contained 4.8×10³ copies of purified human genome, and wherein components had been mixed so as to attain the concentrations of Table 8 below, PCR and Tm analysis were performed using SMART CYCLER (manufactured by Takara Bio Inc.). The conditions of PCR and Tm analysis are as shown in Table 9 below. In Tm analysis, Optics was set to Ch1.

The substrates (*1) were dNTPmix. The composition of dNTPmix was dATP, dCTP, dGTP and dTTP.

The enzyme (*2) was Tth or modified Tth; Tth represents a wild type Tth polymerase wherein the amino acids at positions 1 to 291 have been deleted; and modified Tth represents a Tth polymerase wherein P653E mutation has been introduced and wherein the amino acids at positions 1 to 291 have been deleted.

TABLE 8

| Total Amount of Reaction Solution: 25 μl | |
|---|---|
| 1 × buffer 2 (for High Fidelity) | |
| Substrates (*1) | 200 nM |
| Probe | 200 nM |
| Forward Primer | 500 nM |
| Reverse Primer | 1000 nM |
| Purified Genome | 4800 copies |
| Enzyme (*2) | 700 ng |

TABLE 9

| Conditions of PCR and Tm Analysis |
|---|
| 95° C. for 60 sec |
| ↓ |
| (95° C. for 5 sec, 68° C. for 420 sec) × 35 |
| ↓ |
| 68° C. for 420 sec |
| ↓ |
| 95° C. for 10 sec |
| ↓ |
| 40° C. for 60 sec |
| ↓ |
| Tm (40° C. → 85° C., 1° C./sec) |

Figure 3A:
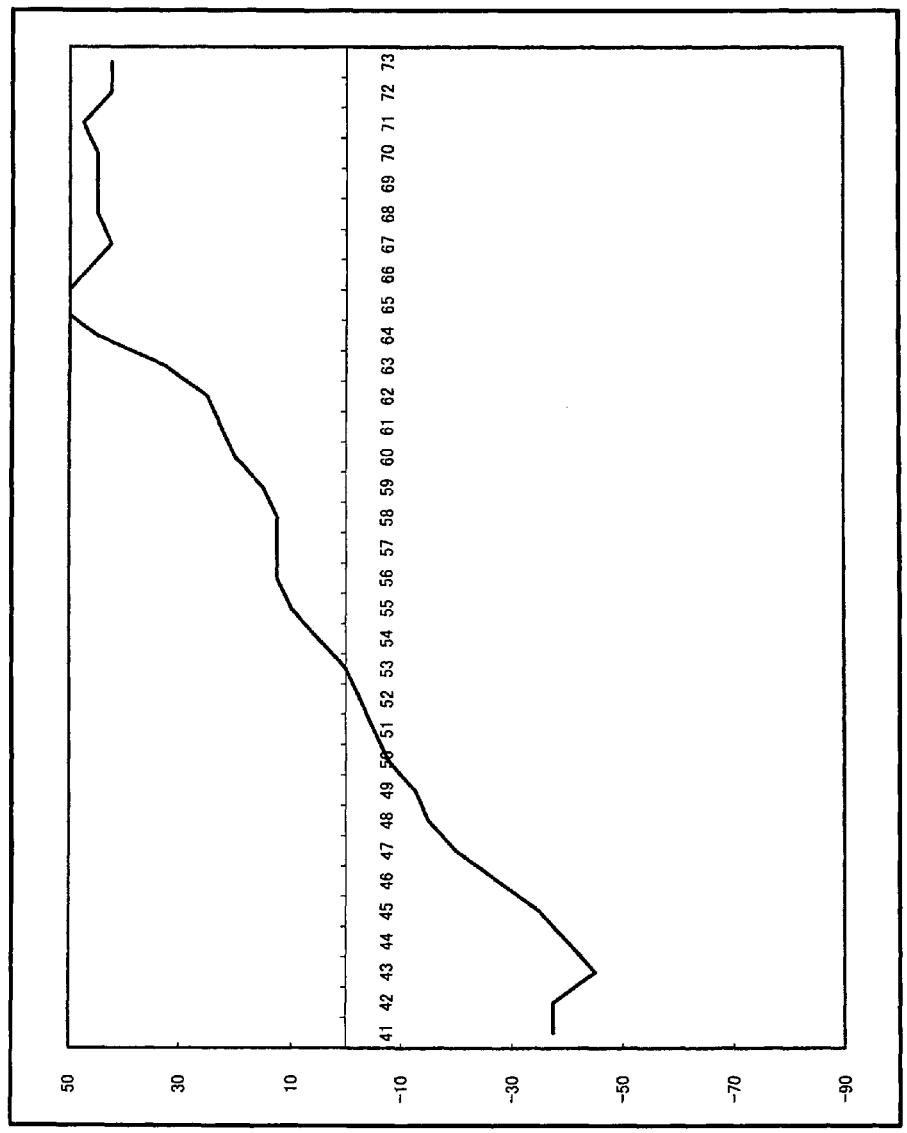
FIG. 3 shows the change in Tm analysis for a CYP2D6 gene in the amount of the change in the fluorescence intensity per unit time (−(Amount of Increase in Fluorescence Intensity)/t) in cases where dNTPmix as the substrates and Tth (FIG. 3A) or modified Tth (FIG. 3B) were used, in Example 3. The ordinate represents the amount of the change in the fluorescence intensity per unit time (−d(Amount of Increase in Fluorescence Intensity)/t), and the abscissa represents the temperature (° C.).
Figure 3B:
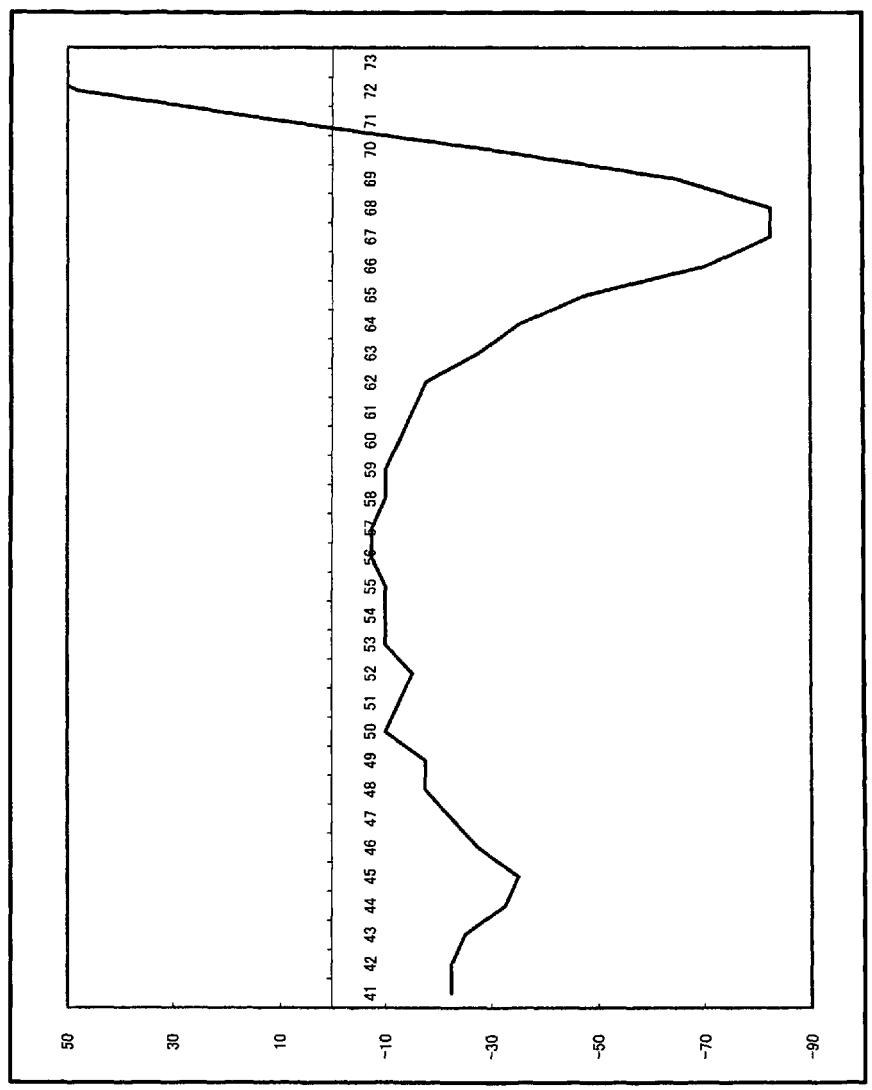

In case of Tth, there was no detection peak after amplifying a long chain of 5.1 kbp that could be confirmed (FIG. 3A); while, in case of modified Tth, a detection peak was confirmed (FIG. 3B). From the fact that the amplification of 5.1 kbp was attained for 420 seconds, it is found that the amplification of the polynucleotide at about 12 bp/sec can be attained.

The invention claimed is:

1. A method of amplifying a polynucleotide, comprising:
   (a) mixing primers for amplifying the polynucleotide, a polymerase, nucleotide substrates and a template polynucleotide, and
   (b) amplifying the polynucleotide by polymerase reaction,
   wherein the polymerase has an amino acid sequence with at least 85% sequence identity to SEQ ID NO: 1 and has an amino acid residue corresponding to position 653 of the amino acid sequence of SEQ ID NO: 1 replaced with glutamic acid.

2. A method of amplifying and detecting a polynucleotide, comprising:
   (a) mixing primers for amplifying the polynucleotide, a polymerase, nucleotide substrates, a probe for detecting the amplified polynucleotide and a template polynucleotide,
   (b) amplifying the polynucleotide by polymerase reaction, and
   (c) detecting the polynucleotide by using the probe,
   wherein the polymerase has an amino acid sequence with at least 85% sequence identity to SEQ ID NO: 1 and has an amino acid residue corresponding to position 653 of the amino acid sequence of SEQ ID NO: 1 replaced with glutamic acid.

3. The method according to claim 2, wherein the detecting step (c) is carried out by detection of amplified polynucleotides accumulated during the amplification reaction in the amplifying step (b) or by melting curve analysis.

4. The method according to claim 1, wherein the polynucleotide is DNA or RNA.

5. The method according to claim 4, wherein the amplifying step (b) is carried out by PCR or RT-PCR.

6. The method according to claim 1, wherein the nucleotide substrates comprise deoxyuridine triphosphate.

7. A method of amplifying a polynucleotide, comprising:
   (a) mixing primers for amplifying the polynucleotide, a polymerase, nucleotide substrates and a template polynucleotide, and
   (b) amplifying the polynucleotide by polymerase reaction,
   wherein the polymerase is a modified Tth polymerase having an amino acid sequence with at least 85% sequence identity to SEQ ID NO: 1, and having an amino acid residue corresponding to position 653 of the amino acid sequence of SEQ ID NO: 1 replaced with glutamic acid, and
   one or more of the amino acids at the N-terminal side have been deleted to delete or reduce the 5'→3' exonuclease activity.

8. The method according to claim 7, wherein the polymerase is a modified Tth polymerase wherein the amino acids at positions 1 to 77 of SEQ ID NO: 1 have been deleted.

9. A method of amplifying a polynucleotide, comprising:
   (a) mixing primers for amplifying the polynucleotide, a polymerase, nucleotide substrates and a template polynucleotide, and
   (b) amplifying the polynucleotide by polymerase reaction,
   wherein the polymerase is a modified Tth polymerase comprising the amino acid sequence of positions 292 to 834 of SEQ ID NO: 1, except that an amino acid residue corresponding to position 653 of SEQ ID NO: 1 is replaced with glutamic acid.

10. The method according to claim 1, wherein the polynucleotide amplified in the step (b) has a nucleotide length of not less than 600 nucleotides.

11. The method according to claim 1, wherein the polymerase comprises the amino acid sequence of SEQ ID NO: 1, except that an amino acid residue corresponding to position 653 of the amino acid sequence of SEQ ID NO: 1 is replaced with glutamic acid.

12. The method according to claim 2, wherein the polymerase comprises the amino acid sequence of SEQ ID NO: 1, except that an amino acid residue corresponding to position 653 of the amino acid sequence of SEQ ID NO: 1 is replaced with glutamic acid.

13. The method according to claim 1, wherein the polymerase consists of the amino acid sequence of SEQ ID NO: 1, except that an amino acid residue corresponding to position 653 of the amino acid sequence of SEQ ID NO: 1 is replaced with glutamic acid.

14. The method according to claim 2, wherein the polymerase consists of the amino acid sequence of SEQ ID NO: 1, except that an amino acid residue corresponding to position 653 of the amino acid sequence of SEQ ID NO: 1 is replaced with glutamic acid.

15. The method according to claim 1, wherein the polynucleotide comprises N-acetyltransferase 2 gene.

16. The method according to claim 1, wherein the polynucleotide comprises SWlnfH1 nucleotide region.

17. The method according to claim 1, wherein the polynucleotide comprises Cytochrome P450 2D6 (CYP2D6) gene.

18. The method according to claim 1, wherein the primers comprise
(i) a forward primer consisting of SEQ ID NO: 3 and a reverse primer consisting of SEQ ID NO: 4,
(ii) a forward primer consisting of SEQ ID NO:6, and a reverse primer consisting of SEQ ID NO: 7, or
(iii) a forward primer consisting of SEQ ID NO: 9 and a reverse primer consisting of SEQ ID NO: 10.

19. The method according to claim 2, wherein the polynucleotide comprises N-acetyltransferase 2 gene, SWlnfH1 nucleotide region, or CYP2D6 gene.

20. The method according to claim 2, wherein the primers comprise
(i) a forward primer consisting of SEQ ID NO: 3 and a reverse primer consisting of SEQ ID NO; 4, and the probe consists of SEQ ID NO: 2,
(ii) a forward primer consisting of SEQ ID NO: 6 and a reverse primer consisting of SEQ to NO: 7, and the probe consists of SEQ ID NO: 5, or
(iii) a forward primer consisting of SEQ ID NO: 9 and a reverse primer consisting of SEQ ID NO: 10, and the probe cconsists of SEQ ID NO: 8.

* * * * *